United States Patent
Pozniak et al.

[11] Patent Number: 6,045,543
[45] Date of Patent: Apr. 4, 2000

[54] ALIGNMENT INDICATORS FOR USE WITH PERSONAL CARE ARTICLES

[75] Inventors: Jennifer Elizabeth Pozniak, Appleton; John Philip Vukos, Neenah; Georgia Lynn Zehner, Larsen, all of Wis.

[73] Assignee: Kimberly-Clark Worldwide, Inc., Neenah, Wis.

[21] Appl. No.: 08/964,709

[22] Filed: Nov. 5, 1997

[51] Int. Cl.$^7$ .................................................. A61F 13/15
[52] U.S. Cl. .................................... 604/385.1; 604/386
[58] Field of Search .................................. 604/386, 387, 604/389–391, 385.1

[56] References Cited

U.S. PATENT DOCUMENTS

| | | | |
|---|---|---|---|
| 2,477,914 | 8/1949 | Webb | 604/386 |
| 3,089,494 | 5/1963 | Schwartz | 604/386 |
| 4,014,340 | 3/1977 | Cheslow | 604/386 |
| 4,662,875 | 5/1987 | Hirotsu et al. | 604/387 |
| 5,133,707 | 7/1992 | Roger et al. | 604/389 |
| 5,275,588 | 1/1994 | Matsumoto | 604/389 |
| 5,772,649 | 6/1998 | Siudzinski | 604/386 |

*Primary Examiner*—John G. Weiss
*Assistant Examiner*—Dennis Ruhl
*Attorney, Agent, or Firm*—Michael L. Winkelman

[57] ABSTRACT

A fastener system for use with personal care articles including a substrate formed by a bodyside liner and an outer cover. Fastening tabs, including securing elements, are secured to the substrate at opposing sides of the rear portion of the article. First alignment indicia are located on the front portion of the substrate. Second alignment indicia are optionally located on the respective fastening tabs. In use, a user aligns the fastening tabs with the first indicia on front portion, preferably aligning second indicia with the first indicia, and secures the tabs thereto. In this manner, the personal care article is properly fitted to the wearer, with the fastening tabs a predetermined distance from the front edge of the personal care article. The first indicia can comprise e.g. lines extending across the width of the personal care article, or outlines of the distal edges of the fastening tabs. Second indicia can comprise lines extending across at least a portion of the lengths of the fastening tabs. In other embodiments, the indicia on the front portion can comprise at least two groups of outlines of the outer edges of the respective fastening tabs.

33 Claims, 6 Drawing Sheets

ALIGNMENT INDICATORS FOR USE WITH PERSONAL CARE ARTICLES

CROSS REFERENCE TO RELATED APPLICATIONS

Not Applicable

STATEMENT REGARDING FEDERALLY SPONSORED RESEARCH OR DEVELOPMENT

Not Applicable

FIELD OF THE INVENTION

Personal care articles such as infant diapers, training pants, adult incontinence products, and the like are well known. Such articles have achieved a wide acceptance due to their ability to receive and absorb body exudates.

This invention pertains to alignment indicators for use with fastener systems for such articles. The alignment indicators comprise indicia that assist in proper positioning of fastening tabs with respect to the front edge of such a personal care article. In some embodiments, indicia are located on the fastening tabs as well as on the front portion of the personal care article. The indicia are aligned or otherwise suitably oriented when the fastening tabs are secured to the front portion of the personal care article.

BACKGROUND OF THE INVENTION

In general, personal care articles should comfortably fit the body of a wearer. Personal care articles generally have fastening tabs at the rear of the personal care article that extend outwardly and secure to a front portion of the article. For the personal care article to be effective, the fastening tabs should be properly placed on the front portion of the personal care article.

In the past there has been little thought or concern as to the positioning of the fastening tabs with respect to the front edge of the personal care article. One conventional approach to the subject of tab placement includes a pattern of dots or vertically oriented lines. The dots or lines enable a user to ensure that both fastening tabs are secured to the front portion of the personal care article at approximately the same distance from the center of the front portion. After the first fastening tab is secured, the indicia can be utilized to secure the second fastening tab at a corresponding location, horizontally, on the opposing side of the article. Thus the leg openings are ensured of being approximately the same size. Such indicia assist the user in placing the two fastening tabs approximately the same height relative to the front edge of the front portion of the personal care article. However, there is no specific indicia indicating a specific selected location for the fastening tabs relative to the front edge of the front portion of the personal care article.

Proper positioning of a personal care article on a wearer can be difficult. Personal care articles, for example, can be difficult to properly position on the intended wearer due to leg movements or body movements of the wearer. Such movement creates difficulty in affixing the fastening tabs at proper locations. If the fastening tabs are placed too high on the front portion of the personal care article, part of the securing portion may extend beyond the front edge of the front portion of the article, and thus may contact and irritate the skin of the wearer. Such improper placement can also cause improper leg fit and create leg gapping which potentially may cause leakage.

In the instance when the fastenings tabs are placed too low on the front portion of the absorbent article, the leg openings tend to be drawn too tightly, at least at the top front portion of the leg opening. Further, the front edge of the personal care article may roll or gap at the waist due to the lower positions of the fastening tabs. Rolling up of the personal care article can cause discomfort to the wearer and could result in waist gapping and leakage. Therefore, it is important to ensure that the fastening tabs are secured on the front portion of the personal care article at a selected predetermined distance from the front edge.

Further, it is preferred, for proper fit, that the fastening tabs are drawn directly across the front portion of the personal care article, and placed at a proper angle to the front edge. An improper angle can cause twisting of the fastening tab, and improper fit for the personal care article.

SUMMARY OF THE DISCLOSURE

The present invention relates to a personal care article having a front portion including a front edge, a rear portion including a rear edge, and a crotch portion. The personal care article comprises a substrate including an outer cover, and a bodyside liner in facing relation with the outer cover. First and second fastening tabs extend outwardly from the substrate at opposing sides of the rear portion of the personal care article. The first and second fastening tabs include securing elements at the respective inner surfaces of the respective tabs.

In preferred embodiments, indicia on the substrate at the front portion of the personal care article specifically guide a user regarding positioning of the fastening tabs with respect to the front edge when the tabs are secured to the front portion of the personal care article.

In preferred embodiments, indicia on the front portion of the personal care article comprise first indicia, the fastening tabs include second indicia cooperating with the first indicia in specifically guiding a user regarding positioning of the fastening tabs when the fastening tabs are secured to the front portion of the personal care article. The second indicia on each of the fastening tabs generally are aligned with, and overlie respective portions of the first indicia when the fastening tabs are secured to the front portion of the personal care article thus ensuring proper longitudinal alignment of the fastening tabs with respect to the front edge.

In some embodiments, the indicia comprise at least one line extending across the front portion of the personal care article at a predetermined distance from the front edge of the personal care article. In some embodiments, the at least one line is substantially parallel to the front edge of the personal care article. The second indicia can comprise at least one line at least propinquant a distal edge of each fastening tab. The second indicia can be a line on the outer surface of each fastening tab generally extending in a line substantially parallel to the rear edge of the personal care article.

In some embodiments, the second indicia line on the outer surface of each fastening tab, and the first indicia line on the front portion, when in proper alignment, in combination, substantially give the appearance of a single line extending across the fastening tabs and across substantially the entire front portion of the personal care article when the article is secured to the body of a wearer.

In some embodiments, the second indicia extend substantially the entirety of the length of the outer surface of at least one fastening tab.

In some embodiments, the indicia located at the front portion of the personal care article extend across a longitudinal axis which extends through the center of the front, rear, and crotch portions.

In some embodiments, the indicia have a length of at least about 1 inch, preferably a length of at least about 4 inches, and most preferably a length of from about 4 inches to about 6 inches.

In some embodiments, the personal care article includes an absorbent body located between the outer cover and the bodyside liner.

In some embodiments, the first indicia comprise at least two lines parallel to each other, the second indicia comprise at least two lines on each fastening tab parallel to each other, the parallel lines in the first and second indicia on the front portion and on both tabs cooperating with each other to guide a user to bring the lines in the first and second indicia into alignment respectively with each other when the fastening tabs are secured to the front portion of the personal care article, thereby to give the appearance of two parallel lines extending across the fastening tabs and across substantially the entire front portion of the personal care article. The two parallel lines preferably have two different colors.

In some embodiments, the first and second fastening tabs have curvilinear distal edges, the indicia on the front portion of the personal care article representing at least first and second outlines of respective curvilinear distal edges of the fastening tabs. The first and second outlines on the front portion, of curvilinear distal edges, preferably are on opposing sides of the longitudinal axis.

In some embodiments, the indicia represent at least first and second sets of outlines of curvilinear distal edges of the fastening tabs, the first and second sets of outlines being on opposing sides of the longitudinal axis. Each set of outlines preferably comprises a group of at least three outlines spaced transversely across the front portion of the personal care article at a common distance from the front edge, on the respective side of the longitudinal axis.

In some embodiments the indicia comprise a luminescent material having luminescent pigments that absorb light energy and radiate visible light when exposed to ultraviolet light. Such a material can comprise a luminescent paint including phosphors.

In some embodiments, the indicia comprise at least one transverse line extending across the personal care article, the at least one transverse line being substantially parallel to the front edge of the personal care article.

In some embodiments, the indicia comprise at least three spaced parallel lines having at least two different colors.

In some embodiments, the indicia do not indicate, or assist in, the transverse spacing of the fastening tabs when the tabs are secured to the front portion of the personal care article.

In another family of embodiments, the personal care article includes indicia on the substrate at the front portion defining a specific set of locations along a transverse dimension of the front portion, for securement of the fastening tabs onto the front portion of the personal care article.

In some embodiments each fastening tab comprises a tab base having a first width, and a terminal tab element having a second width narrower than the first width, extending from the tab base, each tab base including second indicia extending along an edge thereof and cooperating with the first indicia to guide a user to bring the first and second indicia into alignment with each other when the fastening tabs are secured to the front portion of the personal care article, the first indicia, when so aligned with the second indicia, being spaced from the respective terminal tab elements.

In some embodiments, the first indicia include first and second lines parallel with each other and parallel with the front edge, and the second indicia include third and fourth lines on each tab base parallel with each other, the first and second lines being aligned with the third and fourth lines when the fastening tabs are guidedly secured to the front portion, the terminal tab elements thus being secured to the front portion between, and spaced from, the first and second lines.

Figure 1:
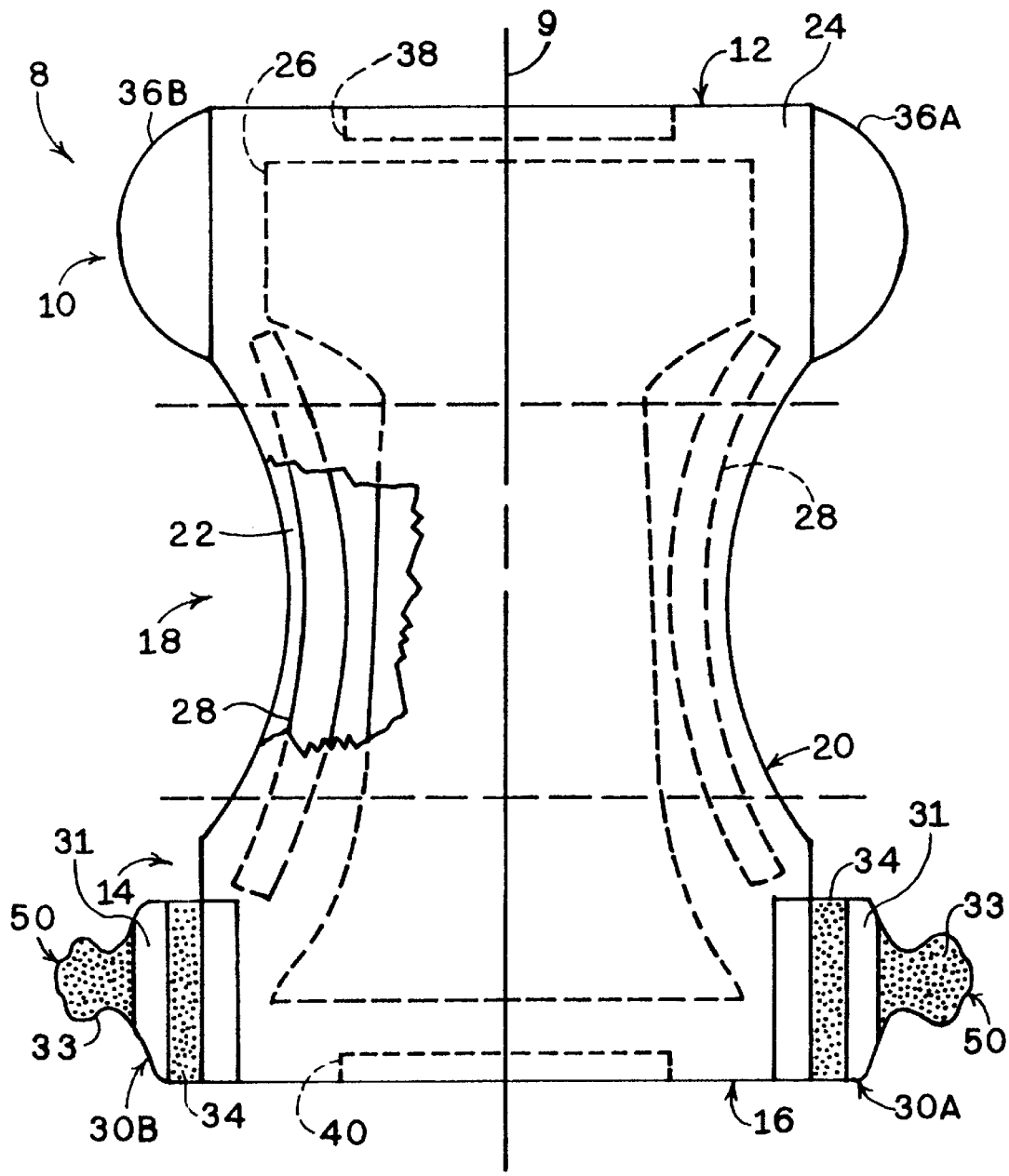
FIG. 1 shows a top plan view of a first embodiment of personal care articles of the invention.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components. The drawings are for purposes of illustration, and are not necessarily drawn to scale.

DETAILED DESCRIPTION OF THE ILLUSTRATED EMBODIMENTS

The various embodiments of the present invention will be described in relationship to their use in disposable personal care articles, but it should be understood that potential uses of the structures of the present invention need not be limited to the context of disposable personal care articles. Other uses for the present invention include other articles, such as caps, gowns, shoe covers, feminine care articles, incontinence garments, and the like.

As used herein and in the claims that follow, the phrase "personal care article" is meant to include adult incontinence articles, feminine hygiene products, articles which have no significant absorbent function, but which receive and/or store urine and/or fecal material, and articles which do have a significant absorbent function, and which receive and/or store urine and/or fecal material.

Figure 2:
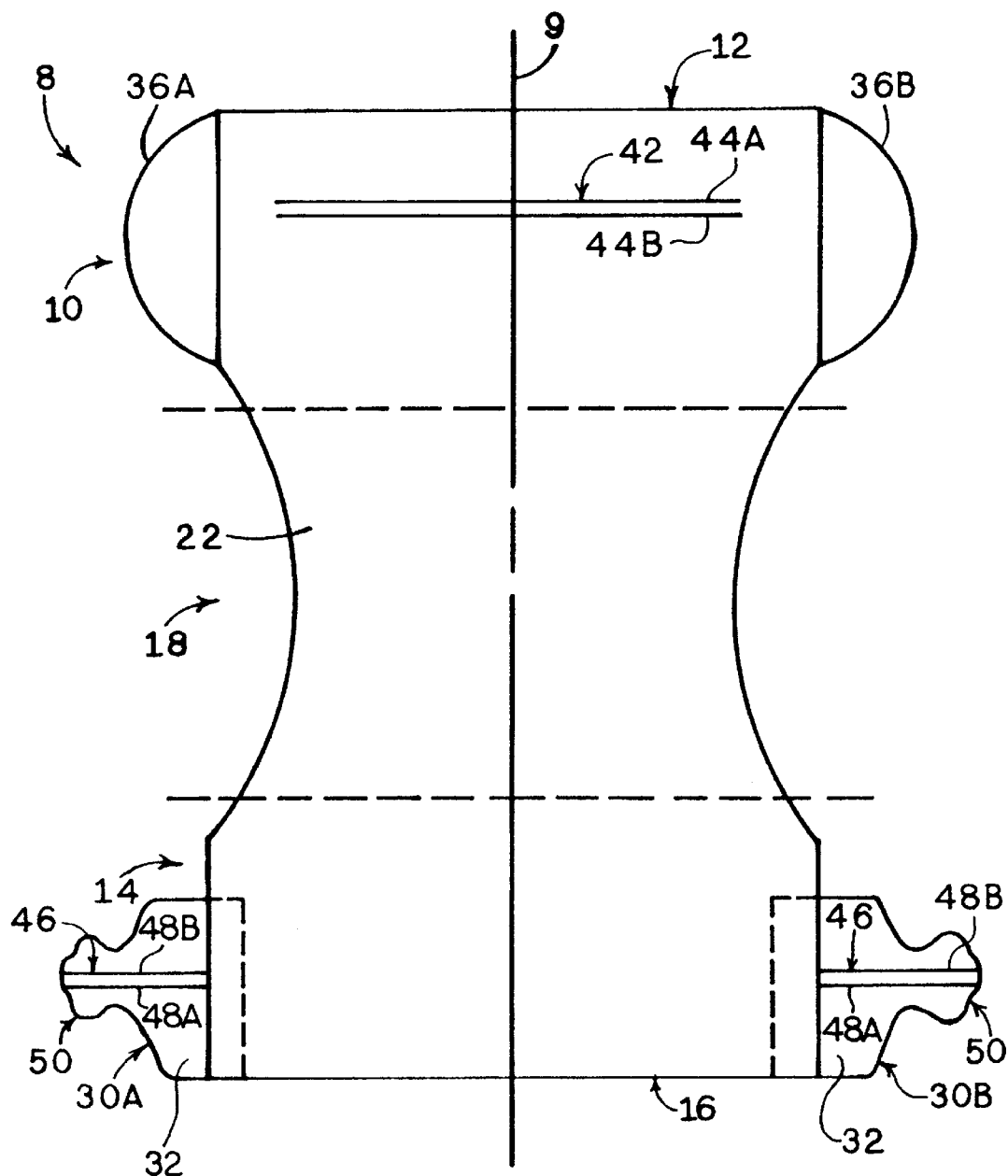
FIG. 2 shows a top plan view of the opposite side, including an outer cover, of the personal care article of FIG. 1.

Personal care article 8 having a longitudinal axis 9, shown in FIGS. 1 and 2, includes a front portion 10 having a front edge 12, a rear portion 14 having a rear edge 16, and a crotch portion 18 between front portion 10 and rear portion 14. Longitudinal axis 9 extends through the center of front portion 10, rear portion 14, and crotch portion 18. Personal care article 8 includes a substrate 20 including an outer cover 22 and a bodyside liner 24 in facing relation with each other. Absorbent body 26 preferably is located between bodyside liner 24 and outer cover 22. Absorbent body 26 receives and retains exudates which pass through bodyside liner 24. Leg cuffs 28 extend longitudinally along opposing outer edges of the crotch portion.

FIG. 1 is a representative plan view of personal care article 8 in its uncontracted state (i.e. in its fully stretched-out condition). The left side of crotch portion 18 of personal care article 8 is cut away to better show outer cover 22 and absorbent body 26. Rear edge 16 is substantially parallel to front edge 12 when personal care article 8 is fully stretched out as in FIG. 1.

In the embodiment illustrated in FIG. 1, fastening tabs 30A, 30B are secured to bodyside liner 24 by ultrasonic bonding at opposing sides of rear portion 14 of personal care article 8. Fastening tabs 30A, 30B extend outwardly from the sides of rear portion 14. Each fastening tab 30A, 30B includes an inner surface 31 and an outer surface 32 (shown in FIG. 2). Each fastening tab 30A, 30B further includes securing elements 33, 34 permanently attached to the fastening tabs at inner surface 31.

Front ears 36A, 36B are secured to substrate 20 by ultrasonic bonding at opposing sides of front portion 10 as shown in FIG. 1.

Waist elastics 38, 40 are located near front edge 12 and rear edge 16, respectively, of personal care article 8.

In use on a wearer, securing elements 33, 34 secure fastening tabs 30A to front portion 10 of personal care article 8, thereby to maintain the article suitably mounted on the wearer. Securing element 33 is located proximate the distal edge of each respective fastening tab 30A, 30B. Additional securing element 34 directly assists securing element 33 in resisting release of fastening tab 30A in spite of forces transferred from rear portion 14 of personal care article 8 and through the fastening tab.

As representatively shown, bodyside liner 24 and outer cover 22 may be generally coextensive and may have length and width dimensions which are generally larger than the dimensions of absorbent body 26. In the illustrated embodiments, bodyside liner 24 is associated with and generally superimposed over the entirety of the surface of outer cover 22, thereby defining the periphery of personal care article 8. Absorbent body 26 is optionally disposed between outer cover 22 and bodyside liner 24 inboard of the periphery of article 8.

FIG. 2 shows a representative plan view of personal care article 8 in its uncontracted state (i.e. fully stretched out) wherein outer cover 22 is the side being viewed. Thus FIG. 2 represents the opposite side of personal care article 8 compared to the view of FIG. 1. First indicia 42 comprise indicia located on outer cover 22 at front portion 10. First indicia 42 comprise lines 44A, 44B extending across front portion 10 substantially in parallel with respect to each other. Parallel lines 44A, 44B are also substantially parallel with respect to front edge 12 of personal care article 8. Parallel lines 44A, 44B are located respective predetermined distances from front edge 12. Parallel lines 44A, 44B are substantially perpendicular with respect to, and extend across longitudinal axis 9. Longitudinal axis 9 tends to divide personal care article 8 into two equal, longitudinally extending sections as shown in FIGS. 1 and 2.

Second indicia 46 are visible at outer surface 32 on respective fastener tabs 30A, 30B. Second indicia 46 comprise first and second substantially parallel lines 48A, 48B extending across substantially the entire length of outer surface 32 of a fastening tab 30A as shown in FIG. 2. Parallel lines 48A, 48B are also substantially parallel to rear edge 16 of personal care article 8. In placing personal care article 8 on a wearer, an installer utilizes second indicia 46, in combination with first indicia 42 as a guide, in fitting the personal care article to a wearer, such that fastening tabs 30A, 30B are positioned a correct predetermined distance from front edge 12 of the personal care article when secured to front portion 10.

Figure 3:
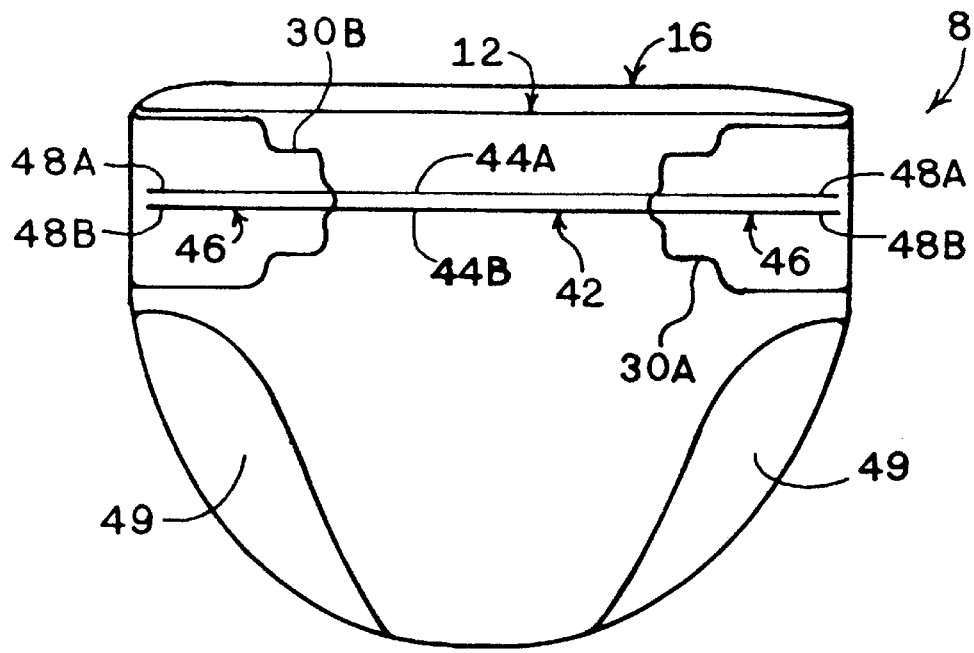
FIG. 3 shows a pictorial view of the personal care article of FIG. 1 having the fastening tabs properly secured to the front portion of the personal care article.

As better illustrated in FIG. 3, fastening tabs 30A, 30B are secured to front portion 10 of personal care article 8 such that lines 44A, 44B of first indicia 42 are aligned with lines 48A, 48B of second indicia 46. In this manner, fastening tabs 30A, 30B are secured to front portion 10 of personal care article 8 at a predetermined distance from front edge 12. Second indicia 46, comprising lines 48A, 48B, may physically overlie a portion of first indicia 42 when fastening tabs 30A, 30B are secured to front portion 10. Therefore, in use, indicia lines 48A, 48B on fastening tabs 30A, 30B and indicia lines 44A, 44B on front portion 10. in combination, substantially give the appearance of a single, preferably uninterrupted pair of lines extending across the fastening tabs and across substantially the entire front portion of personal care article 8. Thus, second indicia 46 assist in locating fastening tabs 30A, 30B a predetermined distance from front edge 12 of personal care article 8 when secured thereto.

Further, when indicia lines 48A, 48B are properly aligned with indicia lines 44A, 44B on front portion, the lines assist in positioning fastening tabs 30A, 30B such that the lengths of the tabs are substantially parallel to front edge 12 of personal care article 8. Thus proper longitudinal alignment of the tabs on the front panel is ensured.

In an embodiment having single first and second indicia lines 44A, 48A (not shown), the combination of indicia lines, when properly placed, resembles a single line extending across fastening tabs 30A, 30B and across substantially the entire front portion 10.

In use, a user can readily install a personal care article 8 on a wearer, with certainty as to the proper position of fastening tabs 30A, 30B. As shown in FIG. 3, the securing of fastening tabs 30A, 30B to front portion 10 encloses, and thus forms, leg openings 49 to correspond in shape to the leg of a wearer.

Outer cover 22 preferably comprises a material which is configured to be substantially impermeable to liquids. For example, a typical outer cover 22 can be manufactured from a thin plastic film, or other flexible liquid-impermeable material.

In some embodiments, outer cover 22 is a polyethylene film having a thickness of from about 0.012 millimeters to about 0.051 millimeters. Alternative constructions of outer cover 22 may comprise a woven or non-woven fibrous web layer which has been totally or partially constructed or treated to impart desired levels of liquid impermeability to selected regions thereof, such as regions that are adjacent or proximate absorbent body 26. Optionally, in some embodiments, an additional outer cover may overlie, or partially overlie, outer cover 22.

Outer cover 22 may optionally be composed of microporous, breathable material that permits vapors to escape from the personal care article while preventing liquid from passing through. For example, a suitable microporous film is a material known as PMP-1, which is available from Mitsui Toatsu Chemicals, Inc. a company having offices in Tokyo, Japan; or polyolefin film known as XKO-8044 and available from 3M Company of Minneapolis, Minn.

In another embodiment of the invention, outer cover 22 can be a nonwoven, spunbonded polypropylene fabric composed or formed into a web. The fabric can be creped or necked such that it is extensible in at least one of the "x" and "y" directions. Other materials having other advantageous characteristics are also useful as outer cover 22. For example, outer cover 22 can comprise a stretch-bonded laminate.

Bodyside liner 24 includes a skin-facing surface which is compliant, soft-feeling, and non-irritating to the wearer's skin. Further, bodyside liner 24 should be sufficiently porous to be liquid permeable, permitting liquid to penetrate through its thickness.

Suitable bodyside liners 24 may be manufactured from a wide selection of web materials, such as porous foams, reticulated foams, apertured plastic films, woven and/or nonwoven natural or synthetic fibers, or a combination of natural and synthetic fibers. Bodyside liner 24 is typically employed to help isolate the wearer's skin from liquids held in absorbent body 26. Various woven and nonwoven fabrics can be used for bodyside liner 24. For example, bodyside liner 24 may be composed of a meltblown or spunbonded web of polyolefin fibers. Bodyside liner 24 may also be a bonded-carded-web composed of natural and/or synthetic fibers.

Bodyside liner 24 may be composed of a substantially hydrophobic and substantially nonwettable material, with the hydrophobic material preferably being treated with a surfactant or otherwise processed to impart a desired level of wettability and hydrophilicity.

In another embodiment of the invention, bodyside liner 24 can be a nonwoven, spunbonded polypropylene fabric composed of fibers formed into a web. The fabric can be creped or necked such that it is extensible in at least one of the "x" and "y" directions.

Bodyside liner 24 may comprise a multiplicity of components, layers, or partial layers, which correspond to any of the materials disclosed herein, as well as others known in the art. The material can be treated with a selected amount of surfactant, such as about 0.28% Trition X-102 surfactant available from Rohm and Haas Corp. of Philadelphia, Penn. The surfactant can be applied by any conventional means such as spraying, printing, brush coating or the like.

Bodyside liner 24 can also comprise a bonded carded web having the necessary characteristics and properties.

In yet another embodiment of the present invention, bodyside liner 24 can comprise a stretch-bonded laminate having appropriate elasticity and width to create general overall surface contact between generally the entirety of the body-facing side of personal care article 8 and the body of a wearer. A stretch-bonded laminate comprises at least a two-layered composite in which one layer is a gatherable layer and the other layer a stretchable layer. The layers are joined together when the stretchable layer is in a stretched condition so that, upon relaxing the composite of the joined layers, the gatherable layer is gathered. The stretchable layer can be a film of stretchable material, such as a layer of styrene ethylene butylene styrene copolymer or other elastomeric polymer, or a plurality of strands of a stretchable material such as latex or LYCRA®. Other materials with similar properties may also, in the alternative, be provided integral with or attached to bodyside liner 24. Such materials should not interfere with the soft texture of bodyside liner 24 against the skin of a wearer.

In embodiments where substrate 20 comprises an extensible outer cover 22 and an extensible bodyside liner 24, indicia 42 generally comprise substantially parallel lines 44A, 44B, when personal care article 8 is fully stretched out. However, when configured for mounting to a wearer, lines 44A, 44B may bend or form a bow shape as a result of the forces on, and changing shape of, substrate 20.

Absorbent body 26 may be manufactured from a wide variety of materials in a wide variety of sizes, and in a wide variety of shapes such as rectangular, trapezoidal, T-shape, I-shape, hourglass shape, etc. The size, and absorbent capacity of absorbent body 26 should be compatible with the size of the intended wearer and the anticipated liquid loading imparted by the intended use of the absorbent body.

Absorbent body 26 suitably comprises a matrix of hydrophilic fibers, such as a web, or webs, of cellulosic fluff, preferably in combination with a high-absorbency material commonly known as superabsorbent material. In a preferred embodiment, absorbent body 26 comprises a mixture of superabsorbent hydrogel-forming material and wood pulp fluff. In place of the wood pulp fluff, one may use synthetic, polymeric, or meltblown fibers or a combination of wood pulp fluff, synthetic fibers, polymeric fibers, meltblown fibers, and/or natural fibers. The superabsorbent material may be substantially homogeneously mixed with the hydrophilic and/or hydrophobic fibers or may be otherwise combined into the absorbent core.

Absorbent body 26 may comprise a laminate of fibrous webs and superabsorbent material, or may comprise other suitable structure operative to maintain superabsorbent material fixed in position at desirable locations in the absorbent body.

The high-absorbency material in absorbent body 26 can be selected from natural, synthetic and/or modified natural polymers and materials. The high absorbency materials can be inorganic materials, such as silica gels, or organic compounds, such as cross-linked polymers. The term cross-linked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

Leg cuffs 28 are formed from separate materials, preferably leg elastics, which are attached to outer cover 22 and/or bodyside liner 24. Materials suitable for forming the leg elastics include LYCRA® strands, ribbons, or one or more layers of a polymeric and/or elastomeric material which may be adhered in personal care article 8, thereby forming leg cuff 28 while the leg cuff material is in a stretched condition. Alternatively, the leg cuff material can be attached to personal care article 8 while the article is pleated and the leg cuff material is in a relaxed condition, such that elastic retractive forces are imparted to leg cuff 28 when the leg cuff is elongated along the length of the personal care article.

In some embodiments, especially where outer cover 22 and bodyside liner 24 are formed from stretchable materials, extensible leg cuffs need not be included in personal care article 8.

Securing elements 33, 34 preferably comprise hook components, such as microhooks, of a hook and loop fastening system. The hook components are employed to secure fastening tabs 30A. 30B to front portion 10 of personal care article 8. Front portion 10 can include loop elements (not shown) mounted in landing zones for securement to the hook components. Preferably, outer cover 22 comprises a material having suitably looped construction that the hook components secure directly to the fabric from which outer cover 22 is made. Such an arrangement reduces the number of elements that must be formed, placed, and secured to personal care article 8. Thus, such an arrangement reduces the cost of producing personal care article 8.

Other types of securing elements 33, 34 besides flexible hook components can be utilized to releasably secure fastening tabs 30A, 30B to front portion 10 of personal care article 8. For example, securing elements 33, 34 can comprise mechanical fasteners, such as the loops, instead of the hooks of a hook and loop fastener system. An attachment surface (not shown) on outer cover 22 then comprises a corresponding hook material in front portion 10, adapted to releasably engage with the loop material of securing elements 33, 34 to hold and retain personal care article 8 on the body of the wearer.

Other well known securing elements can instead be used to support personal care article 8 on the user. For example, a cohesive system, an adhesive fastener system, or the like may be utilized as securing elements 33, 34, with suitable cooperating elements on front portion 10, as necessary, to support personal care article 8 on the wearer.

As shown in FIG. 1, securing elements 33 follow the contour of fastening tabs 30A, 30B at distal edge 50. Rectangularly shaped securing element 34 has a length matching the width of fastening tab 30A where securing element 34 is mounted as part of the fastening tab. The description of fastening tab 30A also describes fastening tab 30B.

Figure 6:
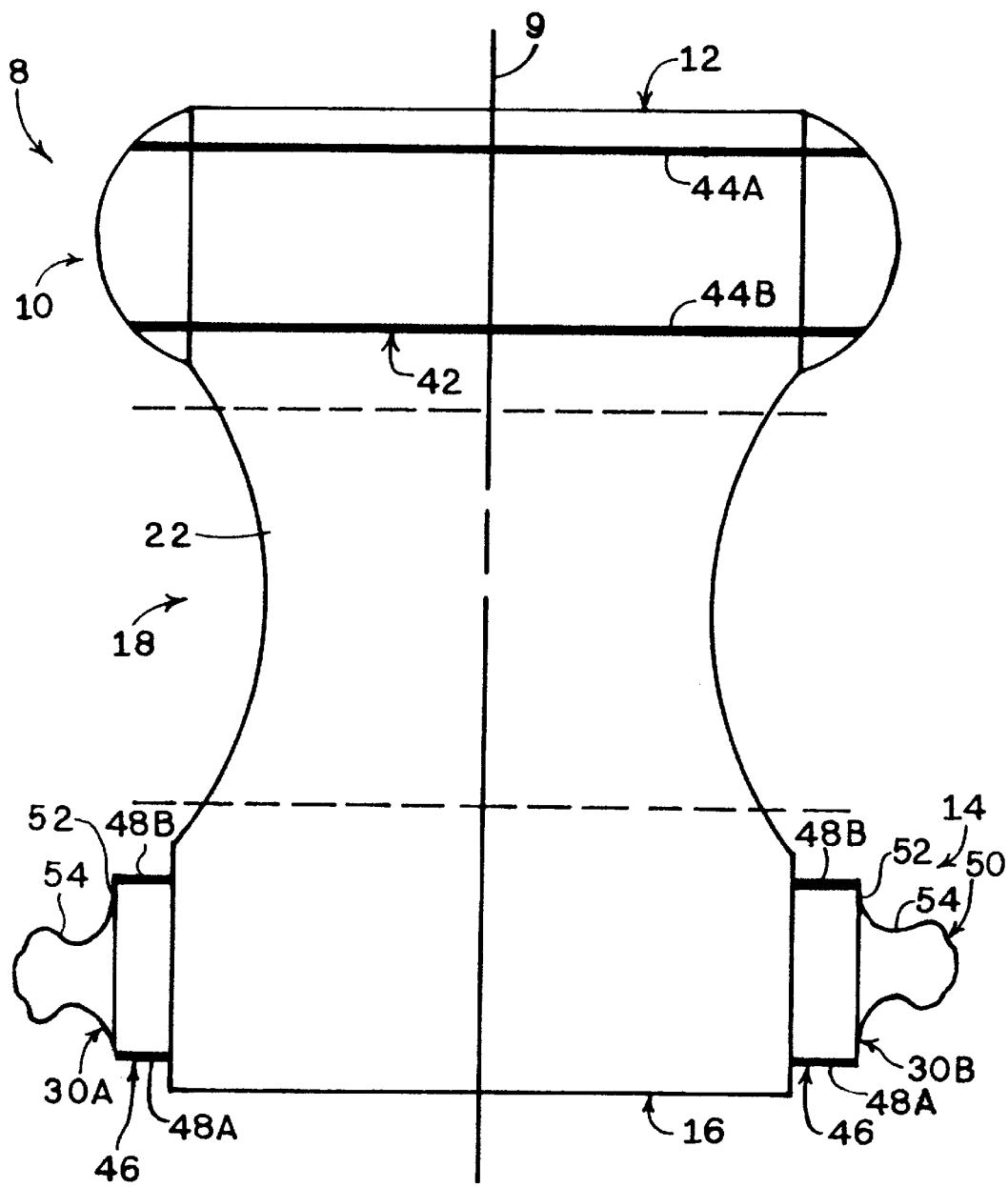
FIG. 6 shows a top plan view of yet another embodiment of personal care articles.

Securing element 34 can be considered an optional element. For example, the embodiment of FIG. 6 is devoid of any second securing element spaced inwardly from the first securing element of the fastening tab.

Fastening tab 30A includes a tab substrate preferably comprising a non-woven material, such as spunbond-meltblown-spunbond material (SMS). Spunbond-meltblown-spunbond material comprises a layer of meltblown material disposed between and in surface-to-surface relationship with the spunbond layers. A fastening tab 30A mode of such SMS material generally is substantially non-extensible during normal usage.

Other materials having suitable characteristics can be substituted for the above described tab substrates for fastening tab 30A. Furthermore, extensible materials can be utilized for the tab substrate.

Many shapes, beyond the shapes illustrated in the drawings, are contemplated for especially distal edge 50 of fastening tab 30A. The fastening tab shapes shown in FIGS. 1–7 are merely for purposes of illustration. For example, fastening tabs 30A, 30B can have a rectangular shape (not shown), and distal edge 50 can comprise a straight line.

While ultrasonic bonding is disclosed as the preferred method for mounting fastening tabs 30A, 30B to substrate 20, other well known methods are contemplated. For example, curing adhesives, stitching, and pressure sensitive adhesives, are all potential mechanisms for suitably and permanently securing the inboard ends of fastening tabs 30A, 30B to substrate 20. As shown in FIG. 1, fastening tabs 30A, 30B are secured to bodyside liner 24 of substrate 20. Other mounting locations, such as between outer cover 22 and bodyside liner 24 can be selected, but are less preferred.

Fastening tabs 30A, 30B can also be formed as an integral part of outer cover 22 and/or bodyside liner 24. Such an arrangement reduces the amount of elements needed to form personal care article 8.

Front ears 36A, 36B can comprise materials similar to those used for bodyside liner 24 and/or outer cover 22. In some embodiments, front ears 36A, 36B are merely an integral extension of bodyside liner 24 and outer cover 22 secured in surface-to-surface relationship with each other. In such embodiments, a separate element bonded to the substrate 20 is not required for forming front ears 36A, 36B.

Waist elastics 38, 40 generally extend about, though not necessarily entirely about, the waist of personal care article 8. Front waist elastics 38 and rear waist elastics 40 generally comprise strands, ribbons or one or more layers of a polymeric and/or elastomeric material which can be adhered in personal care article 8 while both the personal care article and the elastics material are in a stretched condition. Front waist elastics 38 and rear waist elastics 40 can comprise one or more individual strands of elastomeric material, preferably in a spatially separated, generally parallel arrangement of such strands.

Waist elastics 38, 40 preferably are adhesively secured to bodyside liner 24 between the bodyside liner and outer cover 22. In the alternative, waist elastics 38, 40 can be secured to the outer surface of outer cover 22 or the body contacting surface of bodyside liner 24. The placement of waist elastics 38, 40 with respect to the layer or layers which form substrate 20 is not critical to the invention. However, waist elastics 38, 40 should preferably be located close to the respective edges 12, 16.

In some embodiments which comprise stretchable outer covers 22 and/or stretchable bodyside liners 24, waist elastics 38, 40 can be omitted. Thus, in some embodiments, stretchable substrate 20 obviates the need for waist elastics 38, 40 while retaining the respective stretch function.

In some embodiments, opposing left and right spaced containment flaps (not shown) can extend longitudinally along the length of personal care article 8 inwardly of respective side edges of the personal care article. In such embodiments, the containment flaps are typically secured to bodyside liner 24. One example of containment flaps is set forth in U.S. Pat. No. 4,704,116 issued Nov. 3, 1987 to K. Enloe, the disclosure of which is hereby incorporated by reference in its entirety in a manner that is consistent (not contradictory) herewith.

Containment flaps may, for example, be constructed of a fibrous material which is similar to the material comprising outer cover 22. Other suitable conventional materials, such as polymeric films, may also be employed.

Indicia 42, 46 may be configured in various shapes and areas. In the various embodiments, indicia 42 generally comprise lines 44 extending across front portion 10. In embodiments where first indicia 42 comprise lines 44, the lines generally extend at least about 1 inch, preferably at least about 4 inches, and most preferably from about 4 inches to about 6 inches across front portion 10 of personal care article 8. Indicia 46 generally comprise at least one line 48 that is at least propinquant distal edge 50 of fastening tab 30A. Other shapes are contemplated. For example, in the embodiment of FIG. 5, which will be described in detail later, indicia 42 comprise first and second sets of markings having shapes similar to the shapes of fastening tabs 30A, 30B. The markings comprise multiple indicia outlines 43A, 43B on opposing sides of longitudinal axis 9 corresponding to the contours of fastening tabs 30A, 30B at distal edges 50.

As used herein and in the claims that follow, the term "indicia" is meant to include paint, ink, dyes, or other coloring agents applied to, or visible through, substrate 20, as well as separate elements having indicia, such as a separate sheet of material secured to the substrate, colored thread stitched or otherwise secured to the substrate to form the indicia, elastomeric elements having a different color than the substrate and secured thereto, or other elements having substantially the same function and effect, secured to the substrate.

"Indicia" also includes luminescent material such as luminescent paint having luminescent pigments that radiate visible light when exposed to ultraviolet light. Examples of suitable luminescent paints are those made with phosphors, such as zinc or cadmium sulfides.

Figure 4:
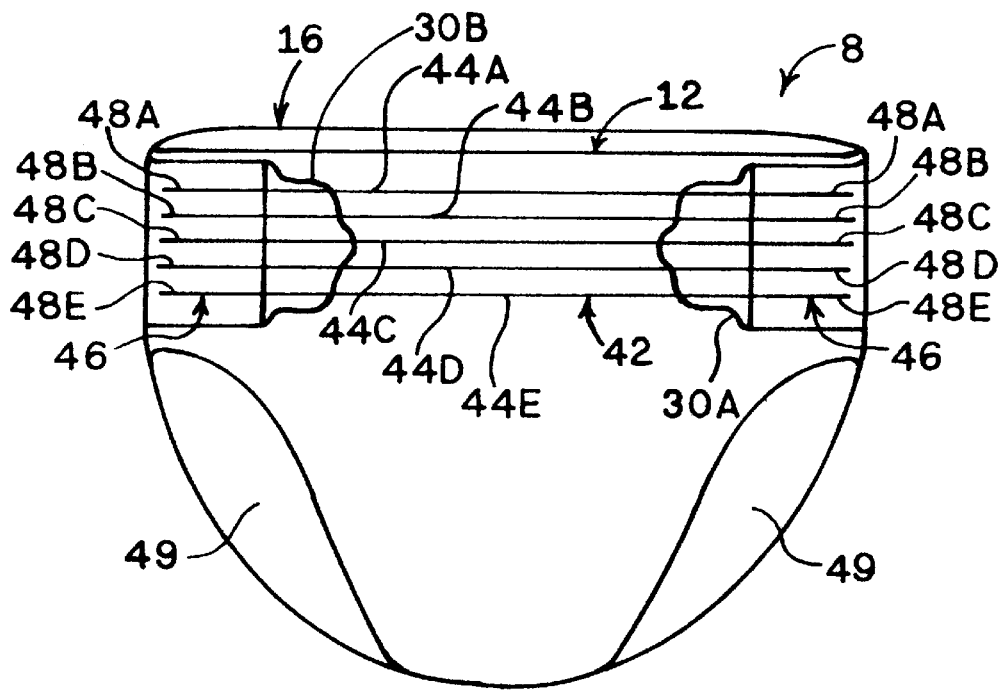
FIG. 4 shows a pictorial view of another embodiment of personal care articles of the invention having multiple indicia.

Indicia 42, 46 preferably have bright colors so that the indicia are easily detected by a user. Indicia 42, 46 preferably greatly contrast in color from the (typically white, light pink, or light blue) color of respective personal care articles. For example, in the embodiment of FIG. 4, first indicia 42 comprise five substantially parallel lines 44A, 44B, 44C, 44D, and 44E. The parallel lines can comprise blue, green, yellow, orange, and red colors, respectively, or any other color combination. Likewise, second indicia 46 on fastening tabs 30A, 30B can comprise five substantially parallel lines 48A, 48B, 48C, 48D, and 48E comprising blue, green, yellow, orange, and red colors, respectively to match respective lines 44A–44E of first indicia 42. Thus in use, as shown in FIG. 4, the person installing personal care article 8 can simply visually align multi-colored lines 48A–48E on fastening tabs 30A, 30B with multi-colored lines 44A–44E at front portion 10 to secure personal care article 8 to the body of a wearer.

Indicia can also be created by embossing or ultrasonic bonding. For example, embossing can darken the existing color of the material being embossed.

As described earlier, by placing the fastening tabs 30A, 30B at the proper position relative to front edge 12 of personal care article, increased comfort, and better utilitarian operation are achieved. When the personal care article is placed on a wearer, and the tabs are secured to the front portion with the second indicia 46 in alignment with first indicia 42, the proper position or distance of fastening tab 30A from front edge 12 is assured.

Figure 5:
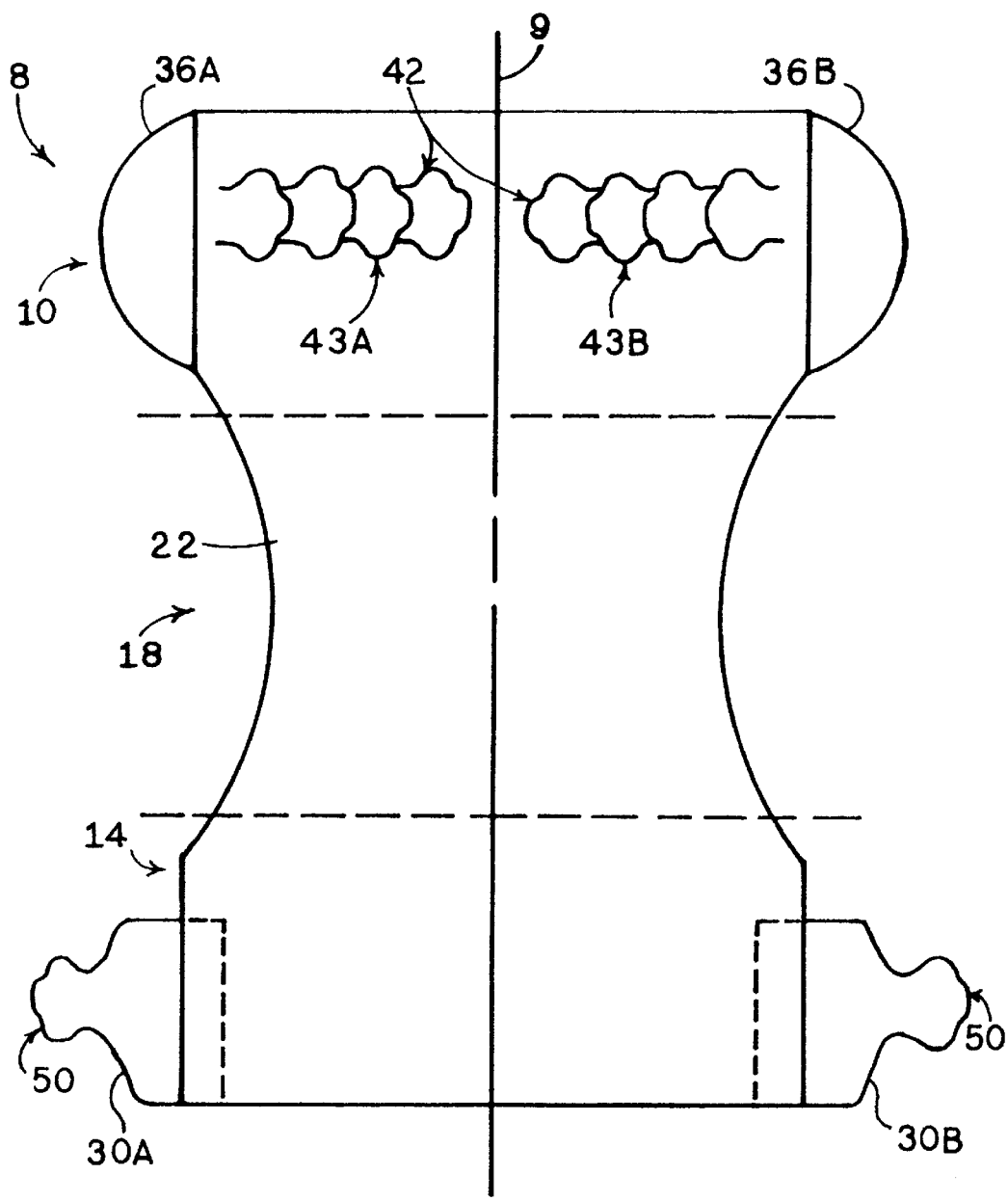
FIG. 5 shows a top plan view of another embodiment of personal care articles of the invention.

In most embodiments, multi-colored lines 48 generally do not indicate transverse spacing of fastening tabs 30A, 30B when the tabs are secured to front portion 10 of personal care article 8. However, such indication of transverse spacing is within the scope of the broadest definition of the invention as illustrated in FIG. 5, and discussed hereinafter.

While FIG. 2 shows the indicia comprising two lines 44A, 44B and FIG. 4 shows the indicia comprising five lines 44A–44E, any number of lines can be utilized. For the embodiments of the invention including lines, at least one line is required for first indicia 42. In such an embodiment, the one line is substantially parallel to, and located a predetermined distance from, front edge 12 of personal care article 8.

Any of the indicia lines may be continuous or discontinuous (e.g. intermittent lines such as dashed lines, or lines of dots). Such discontinuities can apply, for example, to straight lines such as in FIGS. 2–4; and can apply equally well to, for example, curvilinear lines as in, for example, FIG. 5. Other types of indicia can be utilized. For example, the indicia can comprise jagged saw tooth type lines (not shown) extending across front portion 10 of personal care article 8 and onto fastening tabs 30A, 30B. The indicia may comprise sinusoidal type waves (not shown) extending across front portion 10.

Any number of colors can be utilized in indicia 42, 46. For example, in some embodiments, all of the lines can have the same color. However, preferably at least two different colors are present when there are at least two spaced parallel lines forming the indicia.

Embodiments wherein phosphors are utilized in constructing the indicia have numerous advantages. First, assuming a personal care article receives ambient light during the day, its indicia containing phosphors may be visible at night. Second, such personal care articles will be easier to locate at night due to the luminescent effect of the indicia. Therefore, the articles will be easier to locate without operating a light and awakening other persons. Further, less light would be required for placement on a wearer at night. For example, a spent absorbent care article for an infant could be replaced with a fresh absorbent personal care article having luminescing indicia. The amount of ambient light required to secure such fresh absorbent personal care article 8 would be generally less than the amount of light required if such luminescing material were not available. Positioning of fastening tabs 30A, 30B with respect to front edge 12 would be relatively effortless because of using the luminescent indicia to assist in locating and securing fastening tabs 30A, 30B. Therefore, the absorbent personal care article could be changed with minimal disturbance of the wearing infant or other adults, if present in the same room.

If fastening tabs 30A, 30B are inadvertently placed too high on front portion 10, securing elements 33, 34 of the fastening tabs can contact the skin of the wearer and cause irritation to the skin. If fastening tabs 30A, 30B are placed too low on front portion 10, the top portion of leg opening 49 can be too tight on the wearer because of the nonconforming shape of the leg opening. Further, in such instance, substrate 20 at front edge 12 of personal care article 8 could roll because of the improper positioning of fastening tabs 30A, 30B. Therefore, by preselecting and controlling the placement of fastening tabs 30A, 30B with respect to front edge 12 of personal care article 8, these problems can be avoided or at least attenuated.

FIG. 5 shows a plan view of another embodiment of the invention wherein personal care article 8 is in an uncontracted state (i.e. fully stretched out and with all elastic-induced gathering and contraction removed). In FIG. 5, first indicia 42 includes two sets of indicia on front portion 10, on opposing sides of longitudinal axis 9. A first set of indicia 43A corresponds to multiple physical indicia outlines 43A of fastening tab 30A. A second set of indicia 43B corresponds to multiple physical indicia outlines 43B for fastening tab 30B. Each set 43A, 43B of indicia preferably comprises at least three outlines spaced transversely from each other across front portion 10 of personal care article 8, the line of spacing being generally transverse (e.g. perpendicular) to longitudinal axis 9, and at a common distance from front edge 12, sets 43A, 43B being on respective opposing sides of longitudinal axis 9.

Because the outlines in the embodiment of FIG. 5 so resemble the distal edges 50 of fastening tabs 30A, 30B, no indicia is required on the fastening tabs. Fastening tabs 30A, 30B do not require indicia because multiple indicia outlines 43A, 43B follow the contour of fastening tabs 30A, 30B. In use, fastening tabs 30A, 30B are secured to front portion 10 such that the physical outline of distal edge 50 of the fastening tabs is positioned such that the respective distal edge 50 is aligned with an outline of the respective set of outlines. The respective distal edge 50 can, of course, be spaced from the nearest visible (not overlaid) outline so long as the contour of distal edge 50 is equidistantly spaced from, and is in alignment with, the respective outline.

In the embodiment of FIG. 5, distal edges 50 have a curvilinear shape. Therefore distal edges 50 may be considered curvilinear distal edges. The respective sets of outlines 43A. 43B define similar contours or curvilinear shapes corresponding to distal edges 50.

In FIG. 5, multiple outlines of indicia sets 43A, 43B define specific sets of locations along a transverse dimension of front portion 10. Thus fastening tabs 30A, 30B are aligned vertically or longitudinally at preselected distances from front edge 12 of personal care article 8. Fastening tabs 30A, 30B are also properly spaced transversely by the locations defined by the outlines of indicia sets 43A, 43B in this embodiment.

It will be understood by those skilled in the art that the outline elements of sets 43A, 43B may be configured to reflect more than, or less than, the entirety of the outline of distal edge 50, so long as a given outline sufficiently resembles a portion of the outline of the respective tab to enable the same to align a proper portion of the outline of the respective tab with an outline in the respective set 43A, 43B.

FIG. 6 shows a variation of the embodiment of FIGS. 1 and 2. In this embodiment, indicia 42 on front portion 10 comprise first and second parallel lines 44A, 44B spaced substantially parallel to each other. Lines 44A, 44B are also substantially parallel to front edge 12 of personal care article 8.

In the embodiment of FIG. 6, each fastening tab 30A, 30B includes a tab base 52 having a first width, and a terminal tab element 54 having a second width narrower than the first width. Each terminal tab element 54 extends outwardly to a respective distal edge 50 of the respective fastening tab. Each terminal tab element 54 in FIG. 6 includes a securing element (not shown) on the opposite side of the terminal tab element and thus out of view in FIG. 6. Such a securing element can be similar to the securing element described earlier with respect to element 33 in FIG. 1.

Each tab base 52 includes second indicia 46 comprising third and fourth parallel lines 48A, 48B extending along outer edges of the tab base.

Figure 7:
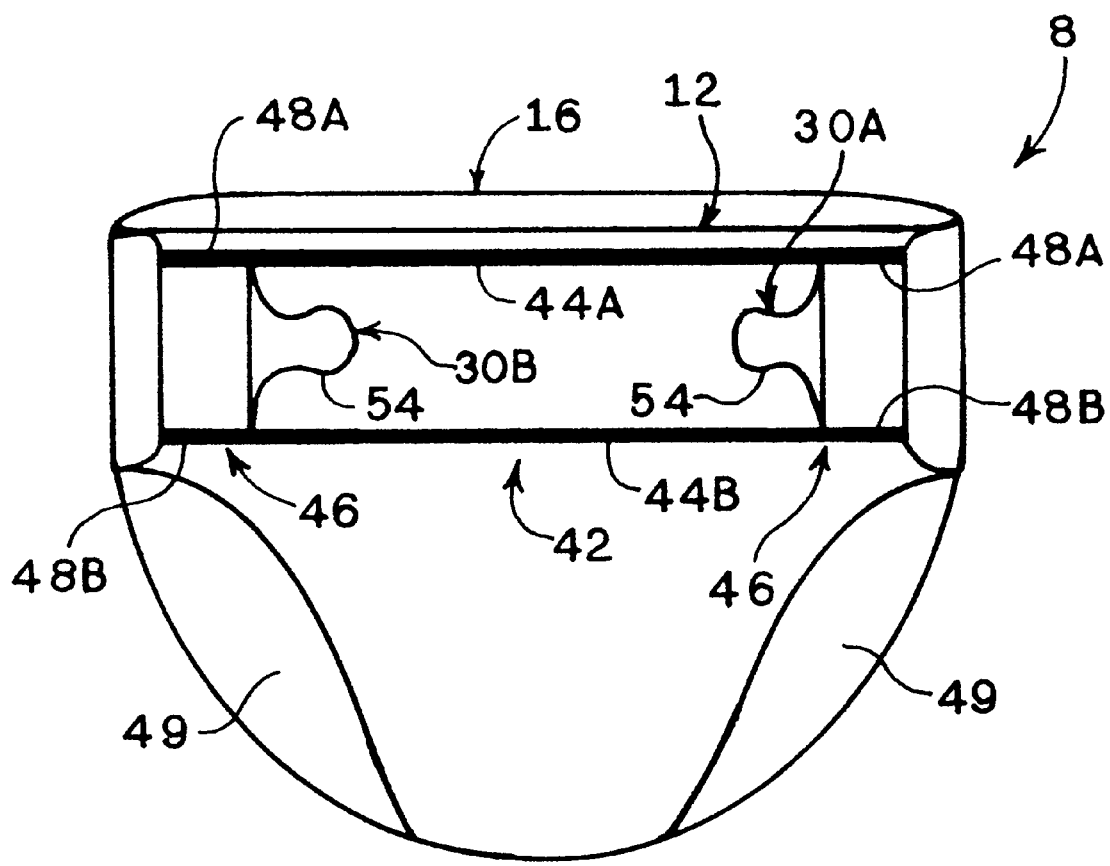
FIG. 7 shows a pictorial view of the personal care article of FIG. 6 having the fastening tabs properly secured to the front portion of the personal care article.

Lines 48A, 48B have colors different from the overall colors of corresponding tab bases 52 whereby lines 48A, 48B are readily visually distinguishable and distinctive against the background colors on the tab bases. In use, third and fourth parallel lines 48A, 48B cooperate with first and second lines 44A, 44B to specifically guide a user to bring the first and third lines into alignment with each other, and correspondingly the second and fourth lines into alignment with each other, when fastening tabs 30A, 30B are being secured to front portion 10 of personal care article 8. When first indicia 42 are aligned with second indicia 46, the first indicia are spaced from terminal tab elements 54. Therefore, as shown in FIG. 7, when fastening tabs 30A, 30B are properly secured, terminal tab elements 54 are located between, and spaced from, parallel lines 44A, 44B of first indicia 42.

The embodiment of FIG. 6, and other embodiments, can be modified such that the indicia extends about distal edge 50 of terminal tab element 54 of fastening tabs 30A, 30B. Thus, in some embodiments, the entire outline of fastening tabs 30A, 30B can comprise indicia.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, such is not meant to include there, or in the instant specification, anything not structurally equivalent to what is shown in the embodiments disclosed in the specification.

Having thus described the invention, what is claimed is:

1. A personal care article having a front portion including a front edge, a rear portion including a rear edge, and a crotch portion, a longitudinal axis extending throuah said front, rear, and crotch portions, said personal care article comprising:

(a) a substrate including an outer cover, and a bodyside liner in facing relation with said outer cover, said substrate having first indicia located at the front portion of said personal care article, said indicia extending across the longitudinal axis, said indicia comprising at least two lines having different colors, said lines being substantially parallel to each other and being substantially parallel to the front edge of said personal care article; and (b) first and second fastening tabs extending outwardly from said substrate at opposing sides of the rear portion of said personal care article, each said fastening tab having an inner surface and an outer surface, said first and second fastening tabs including securing elements at the respective inner surfaces of said respective tabs, near outboard ends thereof.

2. A personal care article having a front portion including a front edge, a rear portion including a rear edge, and a crotch portion, a longitudinal axis extending through said front, rear, and crotch portions, said personal care article comprising:

(a) a substrate including an outer cover, and a bodyside liner in facing relation with said outer cover, said substrate having first indicia located at the front portion of said personal care article, said indicia extending across the longitudinal axis, said indicia comprising at least three spaced parallel lines having at least two different colors, and (b) first and second fastening tabs extending outwardly from said substrate at opposing sides of the rear portion of said personal care article, each said fastening tab having an inner surface and an outer surface, said first and second fastening tabs including securing elements at the respective inner surfaces of said respective tabs, near outboard ends thereof.

3. A personal care article having a front portion including a front edge, a rear portion including a rear edge, and a crotch portion, said personal care article comprising:

(a) a substrate including an outer cover, and a bodyside liner in facing relation with said outer cover, and including first indicia on said substrate at the front portion of said personal care article, said first indicia extending transversely across the front portion; and (b) first and second fastening tabs extending outwardly from said substrate at opposing sides of the rear portion of said personal care article, each said fasteneng tab having an inner surface and an outer surface, said first and second fastening tabs including securing elements at the respective inner surfaces of said respective tabs, each said fastening tab comprising a tab base having a first width, and a terminal tab element having a second width narrower than the first width, extending from said tab base, each said tab base including second indicia extending along an edge thereof, said second indicia cooperating with the first indicia to bring the first and second indicia into alignment with each other specifically guiding a user, fitting said personal care article to a wearer, when said fastening tabs are secured to the front portion of said personal care article, the first indicia, when so aligned with the second indicia, being spaced from the respective terminal tab elements, and said first indicia thereby defining a specific set of locations along a transverse dimension of the front portion, for securement of said fastening tabs onto the front portion of said personal care article.

4. A personal care article as in claim 3, said first indicia including first and second lines parallel with each other and parallel with the front edge, and said second indicia including third and fourth lines on each tab base parallel with each other, said first and second lines being aligned with said third and fourth lines when said fastening tabs are guidedly secured to the front portion, said terminal tab elements thus being secured to the front portion between, and spaced from, said first and second lines.

5. A personal care article having a front portion including a front edge, a rear portion including a rear edge, and a crotch portion, said personal care article comprising:

(a) a substrate including an outer cover, and a bodyside liner in facing relation with said outer cover; and (b) first and second fastening tabs extending outwardly from said substrate at opposing sides of the rear portion of said personal care article, each said fastening tab having an inner surface and an outer surface, said fastening tabs including securing elements on the respective inner surfaces thereof near outboard ends of said respective tabs, each said fastening tab including indicia on the outer surface thereof, said indicia comprising at least one line extending substantially the entire length of the outer surface of each said fastening tab to a distal edge of the respective said fastening tab, said indicia assisting in longitudinal positioning of said fastening tabs with respect to the front edge of said personal care article.

6. A personal care article as in claim 5, said at least one line comprising first and second spaced lines, said first and second spaced lines being parallel to each other.

7. A personal care article as in claim 6, said first and second spaced lines having different colors.

8. A personal care article as in claim 5, said at least one line on the outer surfaces of each said fastening tab being substantially parallel to the front edge of said personal care article when said fastening tabs are secured to the front portion of said personal care article.

9. A personal care article having a front portion including a front edge, a rear portion including a rear edge, and a crotch portion, a longitudinal axis extends through the front, rear, and crotch portions, said personal care article comprising:

(a) a substrate including an outer cover, and a bodyside liner in facing relation with said outer cover, and including indicia on said substrate at the front portion of said personal care article; and (b) first and second fastening tabs extending outwardly from said substrate at opposing sides of the rear portion of said personal care article, each said fastening tab having an inner surface and an outer surface, said first and second fastening tabs including securing elements at the respective inner surfaces of said respective tabs, said indicia representing at least first and second sets of outlines of distal edges of said fastening tabs, the first and second sets of outlines being on opposing sides of the longitudinal axis, said indicia specifically guiding a user in fitting said personal care article to a wearer.

10. A personal care article as in claim 9 wherein said indicia comprises a luminescent material having luminescent pigments that absorb light energy and radiate visible light when exposed to ultraviolet light.

11. A personal care article as in claim 10 wherein said luminescent material comprises a luminescent paint including phosphors.

12. A personal care article as in claim 9 wherein said fastening tabs are curvilinear.

13. A personal care article as in claim 9 wherein each said set of outlines comprises a group of at least three outlines spaced transversely across the front portion of said personal care article at a common distance from the front edge, on the respective side of the longitudinal axis.

14. A personal care article having a front portion including a front edge, a rear portion including a rear edge, and a crotch portion, said personal care article comprising:

(a) a substrate including an outer cover, and a bodyside liner in facing relation with said outer cover, and including first indicia on said substrate at the front portion of said personal care article; and (b) first and second fastening tabs extending outwardly from said substrate at opposing sides of the rear portion of said personal care article, each said fastening tab having an inner surface and an outer surface, said first and second fastening tabs including securing elements at the respective inner surfaces of said respective tabs, said first and second fastening tabs including second indicia which second indicia is in contrast to said fastening tabs, said second indicia cooperating with said first indicia in specifically guiding a user, fitting said personal care article to a wearer, regarding longitudinal positioning of said fastening tabs with respect to the front edge when said fastening tabs are secured to the front portion of said personal care article.

15. A personal care article as in claim 14, said indicia at the front portion of said personal care article comprising first indicia, said first indicia comprising at least a first line substantially parallel to the front edge, said fastening tabs including second indicia, said second indicia comprising at least a second line, cooperating with the first line, to guide a user to bring the first and second lines into alignment with each other when said fastening tabs are secured to the front portion of said personal care article.

16. A personal care article as in claim 15, said first indicia comprising at least two lines parallel to each other, said second indicia comprising at least two lines on each said fastening tab parallel to each other, the parallel lines in said first and second indicia on the front portion and on both said tabs cooperating with each other to guide a user to bring the lines in said first and second indicia into alignment respectively with each other when said fastening tabs are secured to the front portion of said personal care article, thereby to give the appearance of two parallel lines extending across said fastening tabs and across substantially the entire front portion of said personal care article.

17. A personal care article as in claim 16, said two parallel lines having two different colors.

18. A personal care article as in claim 14, said personal care article including a longitudinal axis extending through the center of said front, rear, and crotch portions, said indicia located at the front portion of said article extending across said longitudinal axis.

19. A personal care article as in claim 18, said indicia having a length of at least about 1 inch.

20. A personal care article as in claim 14, said second indicia on each of said fastening tabs being aligned with and overlying respective portions of said first indicia when said fastening tabs are secured to the front portion of said personal care article.

21. A personal care article as in claim 20, said first indicia comprising at least one line extending across the front portion of said personal care article at a predetermined distance from the front edge of said personal care article.

22. A personal care article as in claim 21, said at least one line comprising a first indicia line, said second indicia comprising at least one second indicia line at least propinquant a distal edge of each said fastening tab.

23. A personal care article as in claim 22, said at least one second indicia line on the outer surface of each said fastening tab extending in a line substantially parallel to the rear edge of said personal care article.

24. A personal care article as in claim 23, said at least one second indicia line on the outer surface of each said fastening tab being aligned with said at least one first indicia line, when said article is secured to the body of a wearer, such that said indicia lines on said fastening tabs and the front portion, in combination, substantially give the appearance of a single line extending across said fastening tabs and across substantially the entire front portion of said personal care article.

25. A personal care article as in claim 21, said at least one line being substantially parallel to the front edge of said personal care article.

26. A personal care article as in claim 14 wherein said indicia comprises a luminescent material having luminescent pigments that absorb light energy and radiate visible light when exposed to ultraviolet light.

27. A personal care article as in claim 26 wherein said luminescent material comprises a luminescent paint including phosphors.

28. A personal care article as in claim 14 wherein a longitudinal axis extends through the front, rear, and crotch portions, said indicia representing at least first and second sets of outlines of curvilinear distal edges of said fastening tabs, the first and second sets of outlines being on opposing sides of the longitudinal axis.

29. A personal care article as in claim 28 wherein each said set of outlines comprises a group of at least three outlines spaced transversely across the front portion of said personal care article at a common distance from the front edge, on the respective side of the longitudinal axis.

30. A personal care article as in claim 14 wherein a longitudinal axis extends through the front, rear, and crotch portions, said indicia on said front portion of said substrate representing at least first and second outlines of curvilinear distal edges of said fastening tabs, the outlines being on opposing sides of the longitudinal axis.

31. A personal care article as in claim 14 wherein said first and second fastening tabs have curvilinear distal edges, said indicia representing at least first and second outlines of the curvilinear distal edges of said fastening tabs on the front portion of said personal care article.

32. A personal care article as in claim 14, said second indicia extending substantially the entirety of the length of the outer surface of at least one said fastening tab.

33. A personal care article as in claim 14, said personal care article including an absorbent body located between said outer cover and said bodyside liner.

* * * * *

UNITED STATES PATENT AND TRADEMARK OFFICE
CERTIFICATE OF CORRECTION

PATENT NO. : 6,045,543
DATED : April 4, 2000
INVENTOR(S) : Jennifer E. Pozniak, et al.

Page 1 of 1

It is certified that error appears in the above-identified patent and that said Letters Patent is hereby corrected as shown below:

Column 6,
Line 18, change "10." to -- 10, --

Claim 1,
Line 3, delete "throuah" and insert -- through -- in place thereof.

Claim 3,
Line 11, delete "fasteneng" and insert -- fastening -- in place thereof.

Signed and Sealed this

Thirteenth Day of November, 2001

Attest:

NICHOLAS P. GODICI
Attesting Officer
Acting Director of the United States Patent and Trademark Office